United States Patent [19]

Arnaud et al.

[11] 4,151,836

[45] May 1, 1979

[54] VECTOCARDIOGRAPH APPARATUS FITTED WITH A DEVICE FOR THE ACCURATE PLACING OF THORAX ELECTRODES

[75] Inventors: Pierre Arnaud, Lyons; Robert Guiot-Desvarenne, Caluire, both of France

[73] Assignee: Institut National de la Recherche Medicale, Paris, France

[21] Appl. No.: 846,235

[22] Filed: Oct. 27, 1977

[30] Foreign Application Priority Data

Oct. 28, 1976 [FR] France .................. 76 32679

[51] Int. Cl.² ............................................. A61B 5/04
[52] U.S. Cl. ..................................... 128/644; 128/699
[58] Field of Search ............... 128/2.06 V, 2.06 E, 128/2.06 G, 2.06 R, DIG. 4

[56] References Cited

U.S. PATENT DOCUMENTS 3,043,291  7/1962  Nielsen ............. 128/2.06 E
3,323,514  6/1967  Barrett, Jr. ......... 128/2.06 E
3,534,727  10/1970  Roman ............. 128/2.06 E

FOREIGN PATENT DOCUMENTS 1355600  2/1964  France ............ 128/2.06 E

Primary Examiner—Lee S. Cohen
Attorney, Agent, or Firm—William Anthony Drucker

[57] ABSTRACT

These components comprise a reference frame (3) and a mobile frame (4) mounted slidingly in the plane of the reference frame. After placing electrode E and, consequently, electrode M, which are carried by telescopic arms fixed to the reference frame, the mobile frame is moved in order to place electrodes A and I, fixed to the latter. The correct ratio of distances OE and OM is obtained by reading a fixed scale (37) integral with the reference frame and a mobile scale (45) cooperating with a needle (49) integral with the mobile frame. The mobile scale is articulated (at 451) on a lever mounted pivotally on the reference frame at one end (461) and whose other end bears against a reference backrest (1).

11 Claims, 5 Drawing Figures

VECTOCARDIOGRAPH APPARATUS FITTED WITH A DEVICE FOR THE ACCURATE PLACING OF THORAX ELECTRODES

The invention concerns vectocardiograph apparatus and in particular the accurate placing and correct application of the thorax electrodes which it comprises.

This placing is usually done approximately, without making any measurements, which is a probable source of error.

In an article by Pentti M. Rautaharju, Hermann K. Wolf, William J. Eifler and Henry Blackburn published in *J. Electrocardiology*, Vol. 9, No. 1, 1976, pp. 35-40, it was suggested that these electrodes be placed by means of a dual graduated scale in the form of a set-square applied to the thorax. This manual positioning operation is not very convenient and does not allow all the electrodes to be accurately placed.

The invention puts forward a semi-automatic device for quick, accurate and reliable placing, which also makes it possible to hold the electrodes at a specific pressure during the time the recording lasts.

The vectocardiograph apparatus according to the invention comprises: the five thorax electrodes of the Frank system, viz:

an electrode E designed to be placed on the median anterior point of the thorax;

an electrode M designed to be placed on the median posterior point of the thorax;

an electrode I designed to be placed in the right armpit, at such a point that its respective distances from the posterior plane and the anterior plane be in the ratio of 1/1.2, an electrode A designed to be placed in the left armpit, on the same level as electrode I, and an electrode C designed to be placed near the left nipple, at the end of a line at 45° to the centre of the system;

means of holding these electrodes and applying them to the subject's skin; and components for placing said means in relation to the thorax, and is characterized in that said placing components comprise a reference frame and a mobile frame mounted slidingly in the plane of the reference frame, a reference backrest the slant of which in relation to the frames is adjustable in such a way as to bring the subject's thorax into a direction perpendicular to the plane of the frames; means of adjusting the level and the transversal position of the frames, making it possible to bring electrode E to the desired position on the thorax; the reference frame bearing in the centre of its top front bar a first telescopic segment the inner end of which is connected to means of holding electrode E; the mobile frame bearing on its respective side bars a third and a fourth telescopic segments to whose respective inner ends means of holding electrodes A and I are connected, the third and fourth segments being aligned along an axis perpendicular to the median axis, the mobile frame also bearing on the same side bar as the third segment a fifth telescopic segment slanted at 45° in relation to the third and to the inner end of which means of holding electrode C and means of locating the position of the mobile frame in relation to the reference frame are connected, in such a way as to ensure the correct setting of the position of electrodes A and I by sliding the mobile frame.

In accordance with another feature of the invention, each thorax electrode is housed in a casing shaped to form a housing around the electrode designed to take an absorbent material in order to keep the skin/electrode interface permanently moist.

The advantages and features of the invention will emerge clearly from the following description.

In the attached drawing:

FIG. 1 shows a bed comprising a backrest 1 whose slant is variable and on which a frame-carrying chassis 2 is mounted, slanted at 45° from the horizontal plane.

Figure 1:
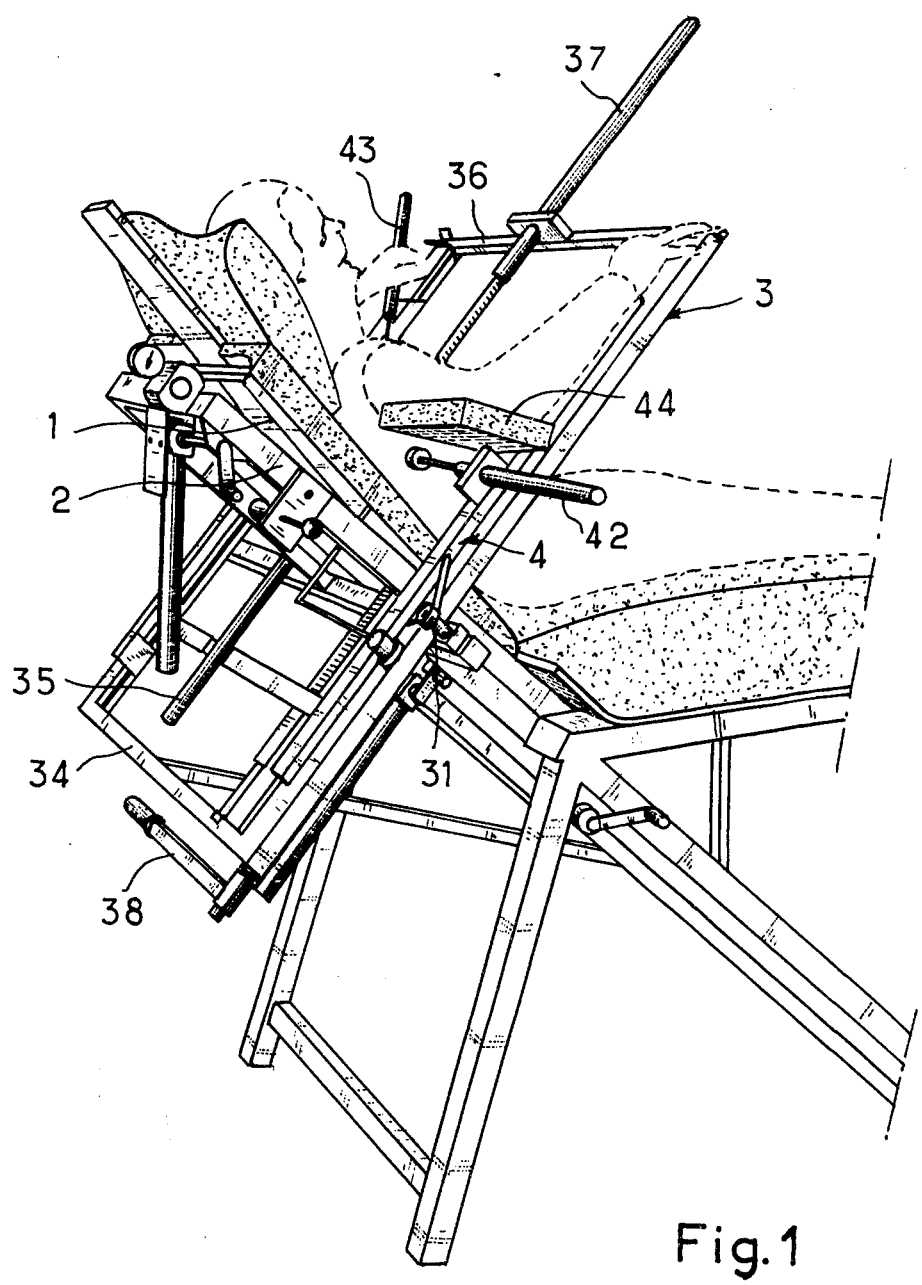
FIG. 1 is a simplified overall view, in perspective, of a device in accordance with a preferred form of embodiment of the invention, given as a non-limiting example.

The chassis 2 carries a first frame 3 and a second frame 4 situated in the same plane slanted at 45° from the horizontal. Frame 3 can slide sideways on chassis 2 so that its median line PP' (FIG. 2) can be brought to intersect the median line of the subject's sternum at E. The amplitude of this movement is limited by stops and a device 31 locks frame 3 in the correct position.

The rear bottom bar 34 of frame 3 bears in its centre a telescopic segment 35 to whose inner end a dorsal electrode/electrode holder unit M is fixed. Arms 35 and 37 are aligned along a median axis of the frame.

In backrest 1 there is a longitudinal slot (FIG. 2) allowing the rod of this dorsal unit to pass. The amplitude of the sideways movement of frame 3 is equal to the width of this slot.

Figure 2:
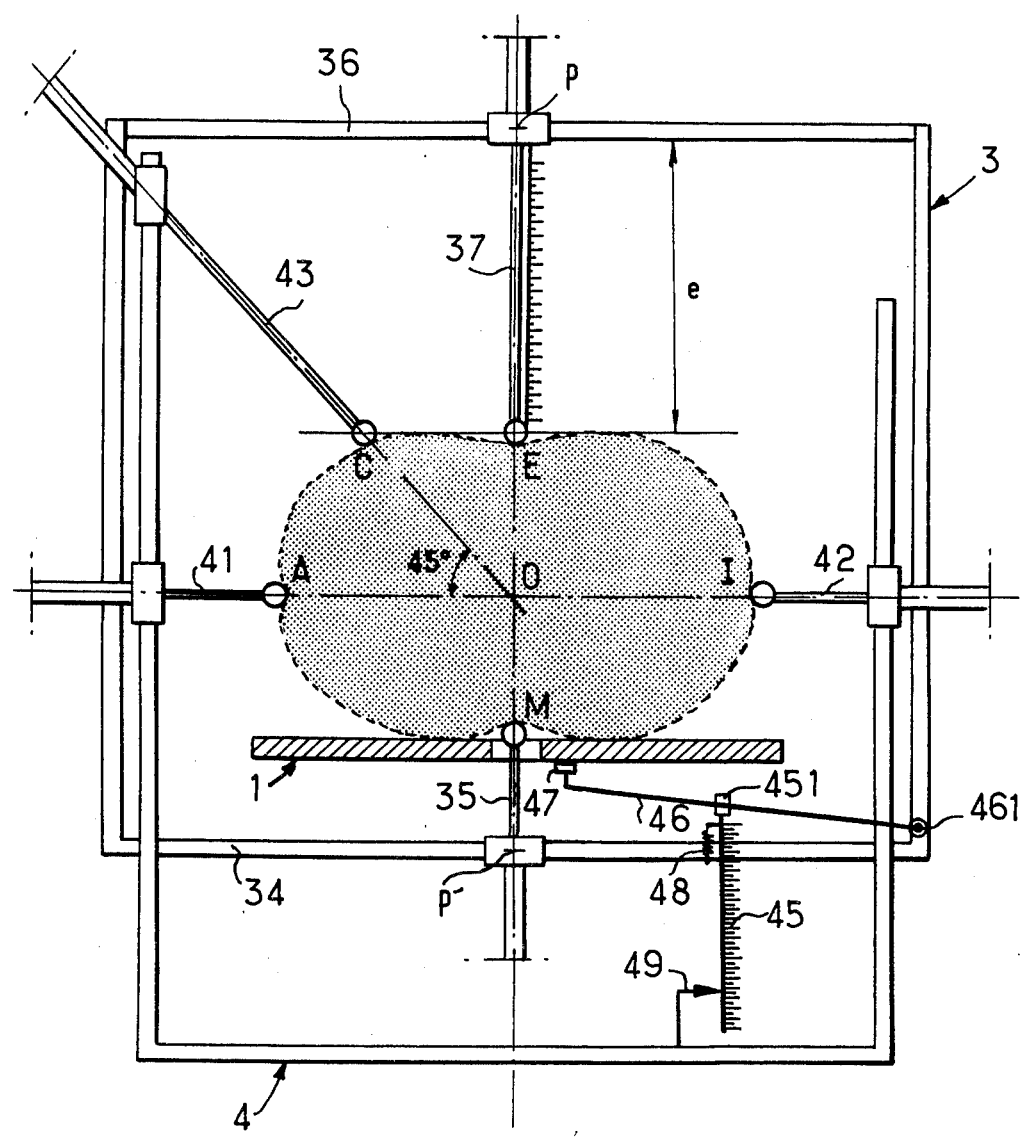
FIG. 2 shows, diagrammatically, the relative arrangement of the electrode-placing frames and the thorax, seen in cross-section in the plane of the frames.

The top front bar 36 of frame 3 bears in the centre a telescopic segment 37 to whose inner end electrode/electrode holder unit E is fixed (FIG. 2). A lever 38 parallel to this bar and situated at the bottom of the frame makes it possible to retract said bar in order to install the subject.

A fixed scale is carried by segment 37 and makes it possible to read PE=e from a distance.

Frame 4 has no top front bar. It slides on frame 3 in the latter's plane by manual control and carries on the side bars telescopic segments to carry and place electrodes A, I and C (41, 42 and 43 respectively).

As can be seen in FIG. 2, the Frank system comprises the following five thorax electrodes, situated in the transversal plane shown:

E: on the median anterior point (sternum)

M: on the median posterior point (column)

I: in the right armpit, at such a point that, if its distance from the posterior plane is equal to 1, its distance from the anterior plane is equal to 1.2

A: in the left armpit, on the same level as I

C: close to the left nipple, at the end of a line slanted at 45° from AI.

Arms 41 and 42 are aligned along an axis perpendicular to axis 35-37, while arm 43 is slanted at 45° in relation to both axes.

As can be seen in FIG. 1, frame 4 carries, on each side, an armrest 44 situated above the armpit segment (42 or 41) and slightly slanted so as to ensure that the arm is well relaxed while at the same time the subject's armpit area is exposed.

In order to place armpit electrodes A and I there is, in addition to the integral fixed scale at point P, a mobile scale 45 (FIG. 2) situated in the plane of the frames and articulated at 451 on a mobile rod 46 which pivots at 461 on frame 3. This rod carries a mechanical feeler 47 which is applied to backrest 1 of the bed. A spring 48, mounted between frame 3 and the mobile scale, pushes the latter upwards.

Articulation point 451 is such that its distance from pivot 461 is in the ratio of $1.2/2.2=0.545$ to the length of rod 46.

A needle 49, fixed to frame 4, moves in front of the mobile scale, the latter itself being guided to undergo a motion of translation. The graduations on the mobile scale are in the ratio of $1/2.2$ to those of the fixed scale and go from front to rear. The origin of the mobile scale is such that if points E, O and M are merged (zero thorax thickness) the two scales show the same value.

The placing of the electrodes is then carried out as follows.

The subject's thorax is placed in the centre of the device and the slant of the backrest is controlled in such a way that its longitudinal axis is perpendicular to the plane of the frames. The arms rest on armrests 44. By sliding the frame-carrier chassis in the direction of the head/foot axis, while maintaining its slant, electrode E is brought to the desired level, e.g. the anterior inner part of the 4th or 5th intercostal space. Frame 3 is then moved sideways by hand so as to bring electrode E to the median point of the thorax (sternum).

Electrode M is simultaneously positioned correctly to the extent that the posterior plane of the thorax is parallel to arm 34. Armpit electrodes A and I then have to be placed, which is achieved by moving frame 4 manually until needle 48 indicates a value equal to value e read on the fixed scale.

In fact, if point M is taken as being fixed, any movement $\Delta E$ of point E along the fixed scale must be translated, in order to preserve the ratio $OE/OM=k$, by a movement in the same direction $\Delta O$ of point O, such as $\Delta E/\Delta O=k+1$. This will be the case in the device described, since the movement of the needle fixed on frame 34, and therefore of point O, measures $\Delta O$ and the indication provided by the fixed scale measures $\Delta E$.

If, now, point E is taken as being fixed, when M moves from $\Delta M$, O must move in the same direction by such a length $\Delta O$ that $\Delta O=k(\Delta M-\Delta O)$. In other words, when $\Delta M=1$ cm, $\Delta O=0.545$ cm. In order for the needle linked to point O to continue to read the same value on the mobile scale despite a movement $\Delta M$, this scale must therefore be moved by $\Delta M/0.545$. This result is approximately obtained with the device described. By way of variant, the mobile scale could be integrated with the movement of one diagonal line of an articulated rhombus wherein the ends of the other diagonal line rested against the backrest and frame 34 respectively. Another variant consists of transmitting the movement of the pick-up to the mobile scale by means of a rack and pinion gear with a suitable ratio.

Figure 3:
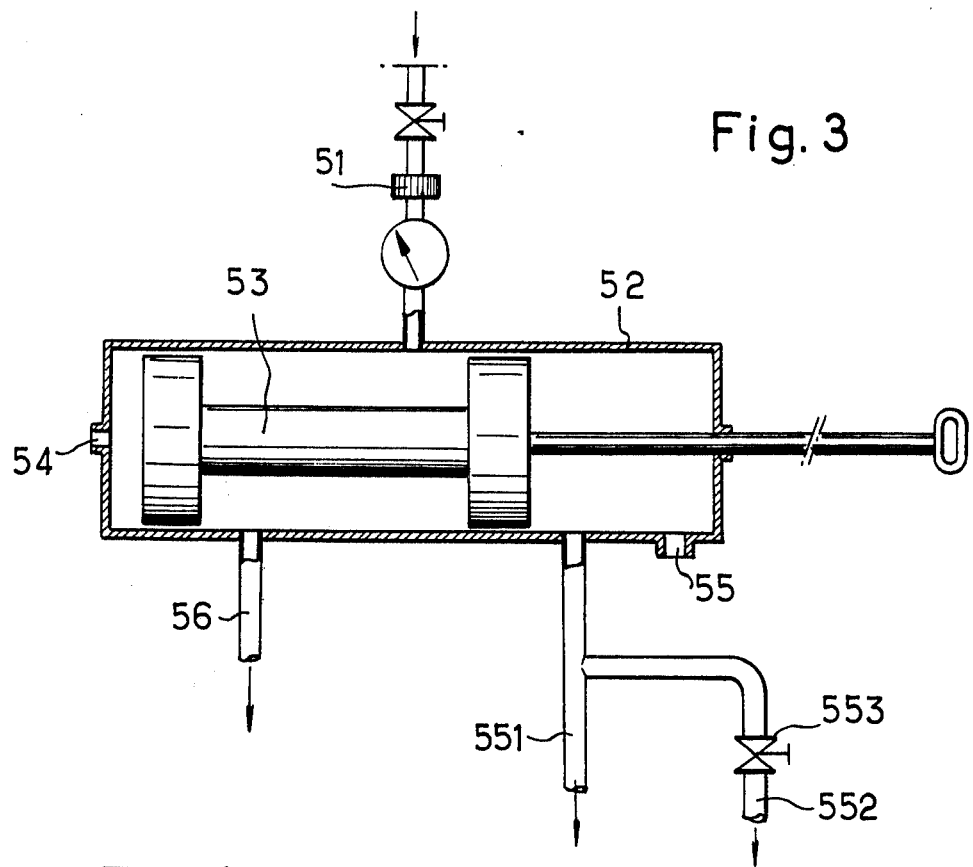
FIG. 3 is a diagram of the pneumatic device controlling the electrode-carrying telescopic segments.
Figure 4:
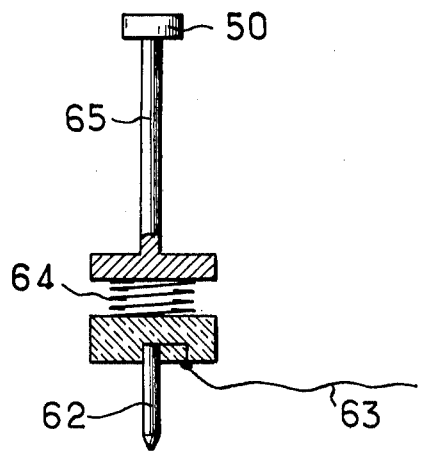
FIG. 4 shows the electrode-carrying component proper.

In order to keep the electrodes applied to the thorax at constant correct pressure during the recording, and then remove them, the pneumatic device shown in FIGS. 3 and 4 is used.

Each of the five telescopic segments includes a cylinder (not shown) in which a piston 50 moves (FIG. 4) which separates two hermetic chambers termed "central" and "distal". There is an intake terminal at each end. Compressed air is distributed to these cylinders as illustrated in FIG. 3. Compressed air, at a pressure set e.g. at 300 g/cm² by means of a serrated wheel 51, comes into the middle of a distribution cylinder 52, in which a double piston 53 moves. At each end of the piston these is an exhaust outlet 54–55. In the inoperative position, shown in the drawing, compressed air is distributed through a single outlet 56 to the five central chambers of the telescopic segments in order to separate the electrodes from the thorax. At the same time, the distal chambers, connected to outlet 551–552 of the distribution cylinder are in free communication with the outside through the exhaust outlet 55 (tubing 551 is connected to the distal chamber of segment 37, while tubing 552 is connected to the four other distal chambers).

In the operating position, compressed air is distributed to the distal chambers in such a way as to apply the electrodes to the thorax, while the central chambers are in free communication with the outside through exhaust outlet 54.

A valve 553 makes it possible to apply electrode E only, which is necessary during the placing operations described above.

By way of variant, the device could be supplied from a source of vacuum.

Figure 5:
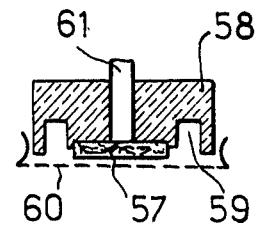
FIG. 5 shows the electrode casing.

FIGS. 4 and 5 show that electrode 57 is contained in a circular insulating casing 58 and surrounded by a circular housing 59. This housing is lined with water-impregnated absorbent cotton wool covered with porous material 60 fixed to the perimeter of the casing. This arrangement makes it possible to maintain permanent moisture on the contact surface between the electrode and the skin without using the customary conductive pastes. Casing 58 is equipped in the centre with a socket 61 welded to the electrode. The corresponding plug 62 (FIG. 4) and its electric cable 63 are fixed to an intermediate insulating component comprised in the electrode-holder device. This component is connected by a spring 64 to a rod 65 itself connected to piston 50. This rod has a certain degree of flexibility, to avoid any untoward incident in case of any untimely movement of the thorax. Spring 64 enables the electrode to be applied correctly to the skin, notably if this is not perpendicular to the rod. Neither the auxiliary components of the installation nor the other electrodes (nape of the neck, left leg, earthing electrode) whose embodiment is outside the scope of the invention, will be described.

Various modifications could be made to the device described and shown without departing from the spirit of the invention.

For example, a device arranged to place the electrodes on a standing subject could be envisaged. A reference backrest to bring the thorax to a position perpendicular to the plane of the frames would still be necessary, but the means of holding the two frames and of adjusting their height and transversal position in order to bring electrode E to the correct position on the subject's sternum could be different from those described.

Moreover, while the reference frame necessarily carries electrode E, while the mobile frame necessarily carries electrodes A, I and C, electrode M can, in principle, be carried either by the mobile frame or by the fixed frame.

We claim:

1. Vectocardiograph apparatus comprising: the five thorax electrodes of the Frank system, said electrodes consisting of:

an electrode E designed to be placed on the median anterior point of the thorax;

an electrode M designed to be placed on the median posterior point of the thorax;

an electrode I designed to be placed in the right armpit, at such a point that its respective distances from the posterior plane and the anterior plane be in the ratio of 1/1.2;

an electrode A designed to be placed in the left armpit, on the same level as electrode I, and an electrode C designed to be placed near the left nipple, at the end of a line at 45° to the centre of the system;

positioning means for placing said electrodes in relation to the thorax, characterized in that said positioning means comprise a reference frame and a mobile frame, said mobile frame being slidably mounted on the reference frame; a reference backrest; and means for supporting the reference backrest and the reference frame and for adjusting the slant of the reference backrest in relation to the reference frame in such a way as to bring the subject's thorax into a direction perpendicular to the said frames; means for adjusting the level and the transversal position of the frames, making it possible to bring electrode E to the desired position on the thorax; the reference frame having a top front bar and a rear bottom bar; a first telescopic segment, being mounted on the said top front bar, at the center thereof and having an inner end; means mounted to said inner end, for holding electrode E; a second telescopic segment being mounted on the said rear bottom bar, at the center thereof and having an inner end, said second telescopic segment being aligned with the first telescopic segment along a median axis of the reference frame; means mountend to the said inner end of the second telescopic segment, for holding electrode M; the mobile frame having first and second side bars; third and fourth telescopic segments respectively mounted on the said first and second side bars and having inner ends; means respectively mounted to said inner ends of the third and fourth telescopic segments, for holding electrodes A and I, the third and fourth telescopic segments being aligned along an axis perpendicular to the median axis of the reference frame, a fifth telescopic segment being mounted on the said first side bar of the mobile frame and slanted at 45° in relation to the third telescopic segment, said fifth telescopic segment having an inner end; means, mounted to the said inner end of the fifth telescopic segment, for holding electrode C and means for locating the position of the mobile frame in relation to the reference frame, in such a way as to ensure the correct setting of the position of electrodes A and I by sliding the mobile frame.

2. Vectocardiograph apparatus according to claim 1, characterized in that said means for locating the position of the mobile frame include a fixed scale mounted to the reference frame and parallel to the first telescopic segment; a mobile scale supported for motion in a direction parallel to the said side bars; a rod pivoted at one end on the reference frame and whose opposite end permanently engages the said backrest close to electrode M; articulation means in said rod, the distance from said articulation means to the pivoting end of the rod being k/k+1 times the rod length, k being the ratio of the distances of axis AI from electrodes E and M; the mobile scale having one end connected to said articulation means; and index means mounted to the mobile frame and cooperating with the mobile scale, the graduations of the two scales progressing in the same direction, those of the fixed scale being in the ratio k+1 to those of the mobile scale and the graduations of both having such origins that the two scales indicate the same value when electrodes E and M are brought into contact with each other.

3. Vectocardiograph apparatus according to claim 1 characterized in that each of the five telescopic segments includes a cylinder and a piston moving in the cylinder and defining a distal chamber and a central chamber on opposite sides of the piston, and by a distributor comprising a cylinder having a first outlet and a conduit connecting the first outlet to the five central chambers of the respective cylinders, a second outlet and first and second conduits connecting the second outlet respectively to the distal chambers of the cylinder corresponding to electrode E and to the distal chambers of the four other cylinders, valve means for controlling the opening of the second conduit, the distributor further having an inlet and first and second exhaust outlets; a source of compressed air being connected to said inlet and piston means movable within the distributor cylinder from a first position in which the first outlet is in fluid communication with the inlet whereas the second outlet is in fluid communication with the second exhaust outlet, to a second position in which the first outlet is in fluid communication with the first exhaust outlet, whereas the second outlet is in fluid communication with the inlet.

4. Vectocardiograph apparatus according to claim 3, characterized by each of the telescopic segments including; a flexible rod having one end integrally mounted to the piston of the telescopic segment; an insulating component and a spring connecting said insulating component to the opposite end of said flexible rod; a plug secured to said insulating component and an electric cable connected to said plug; and a socket cooperating with said plug, said socket having an insulating casing which holds the respective electrode.

5. Vectocardiograph apparatus according to claim 4, characterized in that said casing is shaped to form a circular housing around the electrode, a water absorbent material being lodged in said circular housing, and a porous material covering both the electrode and the housing.

6. Vectocardiograph apparatus according to claim 1, characterized in that the means for adjusting the level and the transversal position of the frames include a chassis on which the reference frame is mounted slidingly in a sideways direction, and means for moving said chassis upwardly and downwardly.

7. Vectocardiograph apparatus comprising: the five thorax electrodes of the Frank system, said electrodes consisting of:

an electrode E designed to be placed on the median anterior point of the thorax;

an electrode M designed to be placed on the median posterior point of the thorax;

an electrode I designed to be placed in the right armpit, at such a point that its respective distances from the posterior plane and the anterior plane be in the ratio of 1/1.2;

an electrode A designed to be placed in the left armpit, on the same level as electrode I, and an electrode C designed to be placed near the left nipple, at the end of a line at 45° to the centre of the system;

positioning means for placing said electrodes in relation to the thorax; characterized in that said positioning means comprise a reference frame and a mobile frame, said mobile frame being slidably mounted on the reference frame; a reference backrest; and means for supporting the reference backrest and the reference frame and for adjusting the slant of the reference backrest in relation to the reference frame in such a way as to bring the subject's thorax into a direction perpendicular to the said frames; means for adjusting the level and the transversal position of the frames, making it possible to bring electrode E to the desired position on the thorax; the reference frame having a top front bar and a rear bottom bar; a first telescopic segment, being mounted on the said top front bar, at the center thereof and having an inner end; means, mounted to said inner end, for holding electrode E; the mobile frame having first and second side bars and a rear bottom bar; a second telescopic segment, being mounted on the said rear bottom bar of the mobile frame, at the center thereof and having an inner end, said second telescopic segment being aligned with the first telescopic segment along a median axis of the reference frame; means, mounted to the said inner end of the second telescopic segment, for holding electrode M; third and fourth telescopic segments respectively mounted on the said first and second side bars and having inner ends; means respectively mounted to said inner ends of the third and fourth telescopic segments, for holding electrodes A and I, the third and fourth telescopic segments being aligned along an axis perpendicular to the median axis of the reference frame, a fifth telescopic segment being mounted on the said first side bar of the mobile frame and slanted at 45° in relation to the third telescopic segment, said fifth telescopic segment having an inner end; means, mounted to the said inner end of the fifth telescopic segment, for holding electrode C and means for locating the position of the mobile frame in relation to the reference frame, in such a way as to ensure the correct setting of the position of electrodes A and I by sliding the mobile frame.

8. Vectocardiograph apparatus according to claim 7, characterized in that each of the five telescopic segments includes a cylinder and a piston moving in the cylinder and defining a distal chamber and a central chamber on opposite sides of the piston, and by a distributor comprising a cylinder having a first outlet and a conduit connecting the first outlet to the five central chambers of the respective cylinders, a second outlet and first and second conduits connecting the second outlet respectively to the distal chambers of the cylinder corresponding to electrode E and to the distal chambers of the four other cylinders, valve means for controlling the opening of the second conduit, the distributor further having an inlet and first and second exhaust outlets; a source of compressed air being connected to said inlet and piston means movable within the distributor cylinder from a first position in which the first outlet is in fluid communication with the inlet whereas the second outlet is in fluid communication with the second exhaust outlet, to a second position in which the first outlet is in fluid communication with the first exhaust outlet, whereas the second outlet is in fluid communication with the inlet.

9. Vectocardiograph apparatus according to claim 8, characterized by each of the segments including a flexible rod having one end integrally mounted to the piston of the telescopic segment, an insulating component and a spring connecting said insulating component to the opposite end of said flexible rod; a plug secured to said insulating component and an electric cable connected to said plug; and a socket cooperating with said plug, said socket having an insulating casing which holds the respective electrode.

10. Vectocardiograph apparatus according to claim 9, characterized in that said casing is shaped to form a circular housing around the electrode, a water absorbent material being lodged in said circular housing, and a porous material covering both the electrode and the housing.

11. Vectocardiograph apparatus according to claim 7, characterized in that the means for adjusting the level and the transversal position of the frames include a chassis on which the reference frame is mounted slidingly in a sideways direction, and means for moving said chassis upwardly and downwardly.

* * * * *